(12) United States Patent
Pari (10) Patent No.: US 9,968,779 B2
(45) Date of Patent: May 15, 2018

(54) APPARATUS FOR ELECTRICAL THERAPIES AND TESTING PROCEDURE FOR ELECTRICAL THERAPY

(71) Applicant: Gilberto Pari, Rimini (IT)

(72) Inventor: Gilberto Pari, Rimini (IT)

(73) Assignee: Gilberto Pari, Rimini (IT)

( * ) Notice: Subject to any disclaimer, the term of this patent is extended or adjusted under 35 U.S.C. 154(b) by 0 days. days.

(21) Appl. No.: 15/028,407

(22) PCT Filed: Oct. 7, 2014

(86) PCT No.: PCT/IB2014/065101
§ 371 (c)(1),
(2) Date: Apr. 8, 2016

(87) PCT Pub. No.: WO2015/052640
PCT Pub. Date: Apr. 16, 2015

(65) Prior Publication Data
US 2016/0250467 A1    Sep. 1, 2016

(30) Foreign Application Priority Data
Oct. 9, 2013   (IT) .............................. RN2013A0042

(51) Int. Cl.
*A61N 1/00* (2006.01)
*A61N 1/36* (2006.01)
(Continued)

(52) U.S. Cl.
CPC ....... *A61N 1/36017* (2013.01); *A61N 1/0551* (2013.01); *A61N 1/36014* (2013.01); *A61N 1/36132* (2013.01); *A61N 1/37241* (2013.01)

(58) Field of Classification Search
USPC .......................................................... 607/62
See application file for complete search history.

(56) References Cited

U.S. PATENT DOCUMENTS 6,381,495 B1   4/2002   Jenkins
6,477,423 B1   11/2002  Jenkins
(Continued)

FOREIGN PATENT DOCUMENTS

EP      2452646 A1      5/2012
WO      2013084026 A1   6/2013

OTHER PUBLICATIONS

Search Report for PCT/IB2014.065101 published Dec. 23, 2014.
Search Report for EP3054882 published May 17, 2017.

*Primary Examiner* — Nicole F Johnson
(74) *Attorney, Agent, or Firm* — Spruce Law Group, LLC (57) ABSTRACT

An apparatus for electrical therapies includes at least one electrocatheter, or an electroneedle, and at least one power supply device capable of electrically supplying the electrocatheter or electroneedle with at least one current suitable for carrying out at least one therapy. The apparatus includes at least one system for testing whether at least one desired point of application of the electrocatheter or electroneedle has been reached in the body of a patient. The testing system includes at least one device for emitting an electric testing current with which to electrically supply the electrocatheter or electroneedle before the start of the therapy, and at least one reading device, capable of providing at least one reading of at least one response generated in the patient by the electrostimulation with the electrocatheter or electroneedle through the testing current.

14 Claims, 5 Drawing Sheets

(51) Int. Cl.
*A61N 1/05* (2006.01)
*A61N 1/372* (2006.01)

(56) References Cited

U.S. PATENT DOCUMENTS

| | | |
|---|---|---|
| 2003/0120328 A1 | 6/2003 | Jenkins et al. |
| 2005/0004562 A1* | 1/2005 | Alcidi ................ A61B 18/1206 606/34 |
| 2005/0222638 A1 | 10/2005 | Foley et al. |
| 2005/0256541 A1 | 11/2005 | Stypulkowski |
| 2006/0247722 A1 | 11/2006 | Maschino et al. |
| 2008/0269836 A1 | 10/2008 | Foffani et al. |

* cited by examiner

APPARATUS FOR ELECTRICAL THERAPIES AND TESTING PROCEDURE FOR ELECTRICAL THERAPY

FIELD OF THE INVENTION

The present invention concerns an apparatus for electrical therapies. By electrical therapies we mean all therapies carried out by administering electrical current to the patient. The present invention has been developed with particular reference to electrostimulation therapies of the nervous system, for example through radio frequency electrical stimuli, however we do not rule out other types of therapies, including possible future electrical therapies that do not produce voluntary lesions of the nervous system. The invention is particularly suitable for stimulating the central nervous system (hereafter for the sake of brevity called CNS), however, in addition or alternatively, this does not rule out other applications, like for example the stimulation of the peripheral nervous system (hereafter for the sake of brevity called PNS). The present invention has also been developed with particular reference to the stimulation of the nervous system of human beings, the anatomy of which will be referred to for the sake of simplicity, however this does not rule out its application to any other living or non-living being, equipped with a nervous system. The present invention also concerns a process for testing the correct positioning of the apparatus.

BACKGROUND

Hereafter we will refer for the sake of simplicity to the electrostimulation of the nervous system, without however excluding the other applications.

In the field it is known to use electrocatheters, i.e. catheters equipped with electrodes, capable of being inserted into the spinal column of an individual and of reaching the spinal root/ganglion complex through the epidural space. Their task is to electrically stimulate such a complex according to what is established by a predetermined therapeutic procedure. Other applications of electrostimulation are known at the level of the PNS. Before proceeding with therapeutic stimulation, it is necessary to check that the electrode is positioned at the desired point, i.e. for example at the preselected ganglion. For this purpose "paraesthesia" is used, i.e. electrical testing stimulations are sent and the patient is asked to tell the doctor when he feels a predetermined sensation.

The effectiveness of such a testing procedure is quite uncertain and causes numerous failures of the subsequent therapy steps. Indeed, the level of sensitivity, and therefore of accuracy, varies from patient to patient based on personal and non-objective characteristics. Moreover, the electrical testing stimulation is at the doctor's discretion, and therefore it could be of a magnitude such as to still provide a response of the patient even when the positioning is poor. This also places the well-being of the subject at risk, since the testing stimulus could not be of the physiologically correct magnitude.

SUMMARY OF THE EMBODIMENTS

A general purpose of the present invention is therefore to completely or partially solve the problems of the prior art.

A preferred purpose of the present invention is to provide an apparatus for electrical therapies capable of carrying out an effective and reliable test of the positioning inside the patient before the therapy starts.

Another preferred purpose of the present invention is to provide an apparatus capable of remaining at least partially inside the patient, for subsequent epidurolysis interventions.

A further preferred purpose of the present invention is to provide an apparatus that allows precise localization of an epidurolysis intervention.

Another further purpose of the present invention is to make the apparatus parts easy to connect and disconnect to/from each other for simple and practical use in the operating theatre.

According to a first general aspect the present invention concerns an apparatus for electrical therapy comprising at least one electrocatheter (most suitable for stimulating the CNS), or an electroneedle (more suitable for stimulating the PNS), and at least one power supply device capable of electrically supplying the electrocatheter or electroneedle with at least a current suitable for carrying out a therapy. The apparatus comprises a system for testing whether the desired point of application of the electrocatheter or electroneedle has been reached, which in turn comprises both at least one device for emitting an electric testing current with which to electrically supply the electrocatheter or electroneedle before the start of the therapy, and at least one reading device. The latter is able to provide at least one reading of at least one response generated in a patient by the electrostimulation with the electrocatheter or electroneedle through the testing current.

Advantageously, therefore, the present invention eliminates the uncertainty of the positioning of the apparatus in the body of the patient, since the reading of the response to the electrical testing stimulus is able to inform the doctor in an objective and not subjective manner when the target has been reached.

In use, the doctor chooses the desired point of application based on the therapy to be delivered, the stimulation through electric current of each point of the body corresponding to a reaction, generally at another point. Knowing the reaction to be expected from the stimulation of the preselected point, the doctor thanks to the invention is able to read it objectively.

Said reading device is preferably able to read at least one type of response of the patient from: a sensitive response, a motor response, a bio-humoral response.

Even more preferably, the reading translates the response into an electrical potential, therefore called evoked or induced potential.

Some examples of response in which translation into an evoked potential is particularly applicable are sensitive responses at the level of the peripheral nervous system, the skin, the muscles, the non-nervous structures, the central nervous system and the brain.

For example, the evoked potentials in such cases are said to be of the somato-sensory (PESS), visual (PEV) and acoustic (PEA) type.

Examples of motor response are contractions, for which reasons in this case the potentials evoked are called muscular and the reading device is for example an electromyograph.

An example of skin response can be sweating.

The reading of the potential evoked can for example be carried out at the level of the skin with simple sensors, thus being non-invasive, or at the level of the nervous system or of the cerebral cortex through needles with electrodes.

In general, this does not rule out the reading of any type of response.

Preferably, the electrocatheter or electroneedle comprises at least one penetration device comprising at least one penetration end equipped with at least one electrode. At least one therapy supply channel carries the therapy current from the supply device to the electrode, a testing power supply channel carried the testing current from the power supply device to the electrode and at least one reading channel carries at least one piece of reading information of the reading device, like for example from at least one sensor to the at least one reading device.

The supply channels and the reading channel are preferably distinct from each other, and in addition or alternatively the supply channels coincide, or partially coincide and in this case one or other is enabled through a switch.

According to some preferred embodiments at least two of the channels are physically joined together at a predetermined point at the penetration device or spaced from it by at least a section of electric cable. This last solution is preferred to allow two operations to carry out the intervention more easily and/or to reduce the weight of the apparatus that bears down directly on the penetration device.

Even more preferably, the joining point coincides with a connection and disconnection point that allows a portion of apparatus comprising the penetration device to be physically separated from the remaining part of the apparatus, so as to be replaced or sanitized for each subsequent operation with obvious advantages in maintaining a sterile environment.

According to a general preferred characteristic, the apparatus comprises at least one data processing device capable of relating at least the testing current and the reading of the response, generating at least one target reached signal and/or an all clear signal to start the therapy, when the relationship reaches a predetermined situation, where preferably the processing device analyses and relates also the time taken by the patient to generate the response to the testing current.

In general, it should be observed that considering the response time in the testing system makes the positioning even more certain, since it avoids considering responses not due to the testing stimulus, even if it is extremely unlikely they will occur.

According to another general preferred characteristic of the invention at least one parameter of the electric testing current can be modified within a predetermined range of values. In this way it is possible to repeat a positioning testing procedure using progressively weaker testing stimuli, promoting the refining of the positioning. It is also possible for the operator to work out whether he is moving towards or away from the target, for which reason he is able to decide in what direction to move the electrocatheter or electroneedle. The apparatus is thus also able to give feedback on distancing.

According to another general preferred characteristic of the invention the electrocatheter or electroneedle comprises at least one end intended to penetrate a patient and to support at least one electrode intended to come into contact with the nervous system to be stimulated, wherein said end extends mainly according to a longitudinal direction and comprises at least one opening for dispensing fluids such as to dispense the fluid in said direction of longitudinal extension. This makes it possible to exploit the precision of positioning of the apparatus also for greater precision of execution of epidurolysis operations, and more generally of administration of any type of drug that is necessary. Preferably, such an opening is exactly at the electrode. For example, such an electrode is position at the distal edge of the end, thus acting as a "tip" perforated with said opening.

According to some preferred embodiments of the invention the testing current has at least one of the following characteristics (more preferably both): from 0.01 V to 10 V (V=Volt) (where 0.1-0.3 V is preferred, for example in the case of use of electromyograph response reading), from 1 to 100 mA (A=Ampere) (more preferably from 20 to 100 mA).

In this case the impedance is preferably between 140 and 700 OHM.

In general the application frequency is preferably less than or equal to 10 Hz, more preferably less than or equal to 3 Hz, where 2 Hz is a preferred value.

The therapy currents could be currents with greater parameter values. In any case, it should be noted that as it stands the therapy currents are in the field of radio frequency, but this does not rule out future applications in which they are in the field of microwaves or higher. A current concrete example is that in which the therapy currents, unlike the stimulus currents, are currents that produce micro-lesions of the nervous system.

According to a second general aspect thereof, the present invention comprises a testing procedure for an electrical therapy, characterised in that before said therapy the correct position of a electrocatheter inside the body of a patient is verified by sending at least one electric testing stimulus to the electrocatheter and reading at least one response caused by such a stimulus with a reading device (for example an evoked potential reader, like an ELECTROMYOGRAPH, PESS, ETC).

Preferably, the procedure comprises the step of relating the testing current and the reading of the response, generating at least one target reached signal, and/or an all clear signal to start the therapy, when the relationship reaches a predetermined situation.

Preferably, it is considered that the target has been reached and/or the reaching of the target is indicated and/or the start of the therapy is allowed only if, as a consequence of a testing current comprised in the following parameters (0.1 V-10 V) (V=Volts) there is a response reading comprised in the range (0.1 mV-1 mV).

Preferably, like for example in the case of reading with an electromyograph, the stimulation current is (0.1 V-0.3 V) and the evoked potential reading is (0.1 mV-0.5 mV).

Indeed, it has been found that these parameters are on the one hand physiologically acceptable and on the other hand give a sufficient guarantee of correct positioning.

In general, it should be observed that in order to consider the target reached and/or to generate said the target reached signal and/or all clear signal to start the therapy, the time taken for the patient to generate the response to the testing current is also taken into consideration, so that if the time is above a predetermined period said target is not considered reached and/or said signal is not generated.

In general, the acceptable response times to allow the therapy can for example be comprised in the range (1-20) milliseconds.

According to a preferred positioning refinement procedure, in verifying the correct positioning of the electrocatheter or electroneedle a first testing stimulus is sent with first predetermined current parameters (First testing current), and if the target is not reached the electrocatheter is repositioned and the procedure is repeated until said target reached signal is obtained; thereafter a second testing stimulus signal that is weaker than the previous one (second testing current) is sent and the procedure is repeated with said second signal, and the procedure is repeated with progressively weaker stimulation signals until a target reached signal and/or all clear signal to start therapy is obtained with a stimulation signal of predetermined minimum magnitude.

In a first general preferred case, the procedure comprises the step of providing at least one power supply device to electrically supply at least one electrocatheter and at least one response reading device, distinct from each other, where before the start of the therapy, "the power supply device supplies the electrocatheter" with a predetermined testing current and the reading device reads at least one response induced by the testing current at at least one predetermined point of the patient, when the reading informs that the electrocatheter is positioned correctly, the therapy is carried out with current sent to the electrocatheter by the power supply device, after the therapy the power supply device and the reading device are physically separated from the electrocatheter that, on the other hand, is kept inside the patient.

According to a second general preferred case, the procedure comprises the step of providing at least one power supply device to electrically supply at least one electrocatheter and at least one response reading device, where before the start of the therapy, "the reading device supplies the electrocatheter" with a predetermined testing current and reads at least one response induced by the testing current at at least one predetermined point of the patient, when the reading informs that the electrocatheter is positioned correctly, before starting the therapy the electrical connection scheme is modified to exclude the power supply of the electrocatheter with the reading device, the therapy is carried out with current sent to the electrocatheter by the power supply device, after the therapy the power supply device and the reading device are physically separated from the electrocatheter that, on the other hand, is kept inside the patient.

According to a third general preferred case, the procedure comprises the step of providing at least one power supply device to electrically supply at least one electrocatheter with a current "and also capable of reading at least one response induced by said current in the patient", wherein, before starting the therapy the power supply device supplies the electrocatheter with a predetermined testing current and reads the response induced by the testing current at at least one predetermined point of the patient, when the reading informs that the electrocatheter is positioned correctly, the power supply device supplies the electrocatheter with a therapy current, after the therapy the power supply device is physically separated from the electrocatheter that, on the other hand, is kept inside the patient.

According to a third general aspect thereof, the invention concerns a consumable portion of an apparatus for electrical therapies comprising at least one penetration device intended to penetrate into a patient and equipped with at least one electrode, characterised in that it comprises at least two from: a power supply port of the electrode with a therapy current, a power supply port of the electrode with a testing current, a port intended to transmit a reading signal of the response of a patient to electrical stimulation.

The term "consumable portion" indicates a portion that can be replaced upon each operation with a new portion, for example for hygiene-sanitation, and not necessarily a portion subject to wear.

Preferably, said consumable portion comprises a selector device to enable the power supply of the at least one electrode from one or other of the therapy and testing power supply ports, as alternatives to each other.

Even more preferably, between the selector device and the at least one electrode there is a single power supply channel.

In general, ports are positioned on a connection interface to one or more electrical power supply devices, where said interface is spaced from said penetration device by at least a section of cable.

Preferably, said ports are positioned on an interface able to be connected and disconnected to/from one or more electrical power supply devices.

BRIEF DESCRIPTION OF THE DRAWINGS

Further characteristics and advantages of the present invention will become clearer from the following detailed description of preferred embodiments thereof, made with reference to the attached drawings and given for indicating and not limiting purposes. In such drawings.

DETAILED DESCRIPTION OF THE EMBODIMENTS

Figure 1:
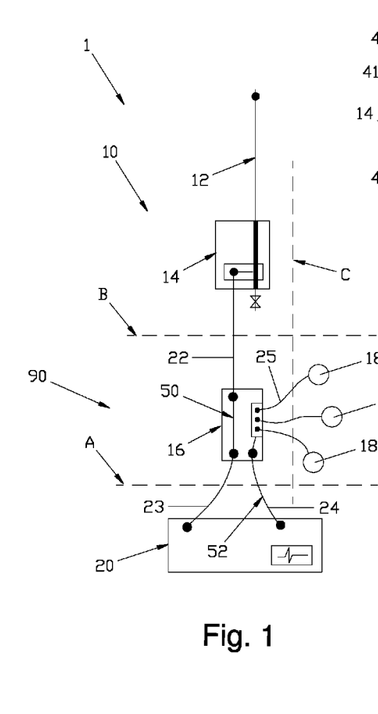
FIG. 1 schematically represents an apparatus for electrostimulation of the nervous system according to the present invention.

With reference to FIG. 1, a first general embodiment of the apparatus for electrostimulation of the nervous system according to the present invention is shown, wholly indicated with reference numeral 1.

The apparatus 1 comprises a electrocatheter 10 (or electroneedle) and an apparatus 20 capable both of delivering at least one electrical therapy current and at least one electrical testing current to supply the electrocatheter or electroneedle and therefore hereafter also called therapy and testing current generating device 20 or power supply device 20. The delivery to the patient of the therapy current and testing current are preferably able to be selectively activated one excluding the other. The apparatus 20 is also able to read at least one response induced by the stimulus with the testing current on the CNS or PNS. Said apparatus for example translates such a reading into an electric potential, called evoked or induced potential.

The reading of an evoked potential typically consists of its conversion into an electric current. However, this does not rule out other forms of reading. The reading of the response can for example be the same as or similar to that of an electromyograph.

It should be observed that the delivery apparatus 20 makes it possible to vary at least one parameter of the testing current, so as to generate electrical testing stimuli that can be selectively varied.

The electrocatheter 10 is the whole of the part represented above the dashed line A, and comprises a penetration device 12, a first electrical interface and support element 14, a second electrical interface element and a plurality of sensors 18 (even just one is sufficient). The electrocatheter is completed with the electrical connection cables 22, 23, 24 and 25, preferably attachable and detachable.

Figures 2, 3, 4:
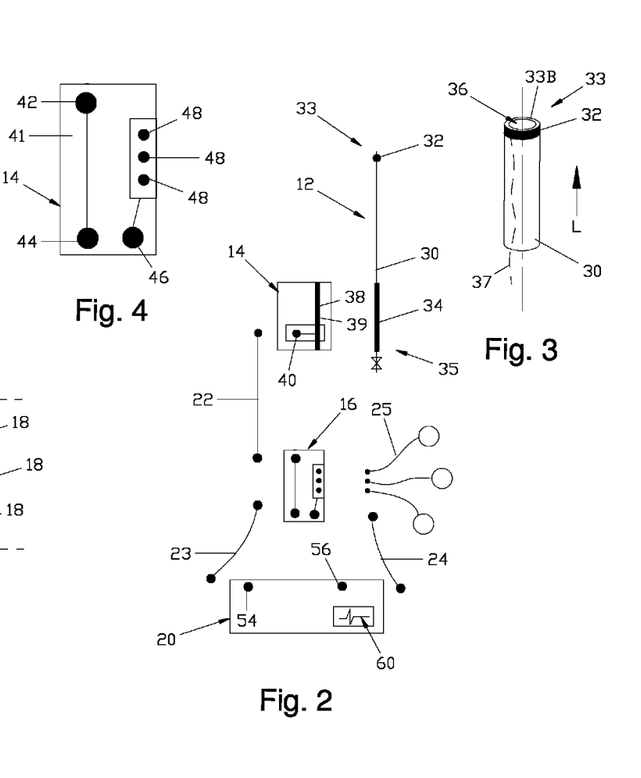
FIG. 2 schematically represents an exploded view of the apparatus of FIG. 1.
FIGS. 3 and 4 schematically represent respective enlarged details of the apparatus of FIG. 1.

With reference to FIG. 2, the penetration device 12 comprises a catheter 30 (or a needle—more suitable for example for the PNS) equipped with at least one electrode 32 at an end thereof 33 intended to penetrate the body of the patient, and for the sake of simplicity called "tip". The electrode 32 is intended to come into contact with the nervous system to be stimulated.

At the opposite end 35, for the sake of simplicity called "tail", the catheter 30 comprises at least one electrical connection port 34, electrically connected to the electrode 32 and intended to electrically connect to the first interface element 14.

As can be seen in the enlargement of FIG. 3, the catheter 30 is hollow, so as to form a duct with an outlet opening 36 at the tip 33 and oriented in the direction of longitudinal extension L of the catheter.

The catheter in this way is able to dispense fluids, for example drugs, through the outlet opening 36 according to said direction of longitudinal extension L.

It should be noted that the electrode 32 is arranged on the end edge 33 *b* of the catheter, actually acting as a penetration tip. In this way the dispensing of the fluid takes place exactly at the electrode and therefore is precise. Preferably, the electrode 32 develops around the opening 36, for example in the form of a perforated cylinder.

FIG. 3 also shows the inner electric cable 37 for the electrical connection between the electrode 32 and the port 34.

With reference again to FIG. 2, the first interface element 14 comprises a housing seat 38 of the catheter 30, that preferably also comprises an electrical connection port 39 intended to couple with the connection port 34 of the catheter 30. As can be seen in FIG. 2 the catheter 30 is able to be physically (and electrically) coupled with and decoupled from the first interface element 14.

The interface element also comprises an electrical connection port 40 able to be coupled and decoupled (physically and electrically) with respect to the cable 22 (from which it receives current) and coupled with the port 39 to supply current to the catheter.

Through the cable 22 the first interface device 14 is able to be electrically and physically connected to and disconnected from the second interface device 16. The electric cable 22 preferably has a length of over 30 cm, more preferably over 50 cm, even more preferably over 1 m.

With reference to FIG. 4, the second interface device 16 comprises a support element 41 on which there are at least one electrical connection port 42 with the first interface device 14, at least two electrical connection ports 44 and 46 with the apparatus 20 and at least one connection port 48 with an electrode 18.

The port 44 is preferably in electrical contact solely with the port 42, so as to form a direct supply bridge between the apparatus 20 and the catheter 30, capable of transmitting both the therapy current and the testing current. Such a bridge is electrically insulated from the port 46, which on the other hand is in electrical connection with the ports 48, so as to electrically interface the sensors 18 with the apparatus 20 so as to read possible evoked potentials generated by the testing current.

With reference again to FIG. 2, the apparatus 20 comprises at least one outlet port 54 of the therapy current and of the testing current, and an inlet port 56 of the reading of the evoked potential.

The cable 23 makes it possible to electrically and physically connect and disconnect the port 44 with respect to the port 54, the cable 24 makes it possible to electrically and physically connect and disconnect the port 46 with respect to the port 56, and the cables 25 make it possible to electrically and physically connect and disconnect the ports 48 with respect to the sensors 18.

As can be seen, therefore, the electrocatheter 10 comprises a first electrical connection channel 50 (indicated in FIG. 1) intended to transmit the supply current from the apparatus 20 to the catheter 30 comprising the port 54, the cable 23, the second support device 16, the cable 22 and the first support device 14. The electrocatheter 10 also comprises a second electrical connection channel 52, distinct from the first, intended to place the apparatus 20 in electrical communication with the sensors 18. It comprises the port 56, the cable 24, the second support device, and the cables 25.

Such channels are physically joined by the second interface device 16, which for this reason is also called "physical connection and electrical ramification point".

Through the port 54, the apparatus is able to transmit at least one testing current, for example comprising an electrical impulse comprised in the following range (0.01-10 V and/or of frequency less than or equal to 10 Hz.

Through the same port the apparatus 20 is able to deliver a therapy current, for example of the type know as current in the field of radio frequency, i.e. with a frequency comprised in the range [30 KHz, 300 GHz] including extremes, and more preferably of the sub-type known as current in the field of microwaves, i.e. with a frequency comprised in the range [300 Mhz-300 GHz] including extremes.

Through the port 56, the apparatus 20 receives from the sensors 18 at least one reading signal of a potential evoked by the testing current. As a consequence of the reading signal the apparatus 20 generates an all clear signal 60 to start the therapy. There are no particular limitations to the all-clear signal, which can simply be the graphical display of the reading signal, as well as a message or an acoustic signal or a light signal.

In the preferred embodiments the apparatus 20 also has the function of a processing device that compares the testing current with the evoked potential and produces an all clear signal based on the result of said comparison. For example, such a comparison can take into account the response time (i.e. the time that passes between the emission of the testing current and the reading of the potential evoked) and/or the magnitude of the testing current and of the evoked potential read.

It is thus clear that the apparatus 20 and the channels 50 and 52 are part of an electrical testing system 90 of the correct positioning of the electrode 32.

It should be observed that preferably the port 54 is dedicated exclusively to the delivery of current whereas the port 56 is dedicated exclusively to the reading of the evoked potential, so that they cannot be operatively exchanged with one another and must be suitably identified to be distinguished by the operator.

Figure 5:
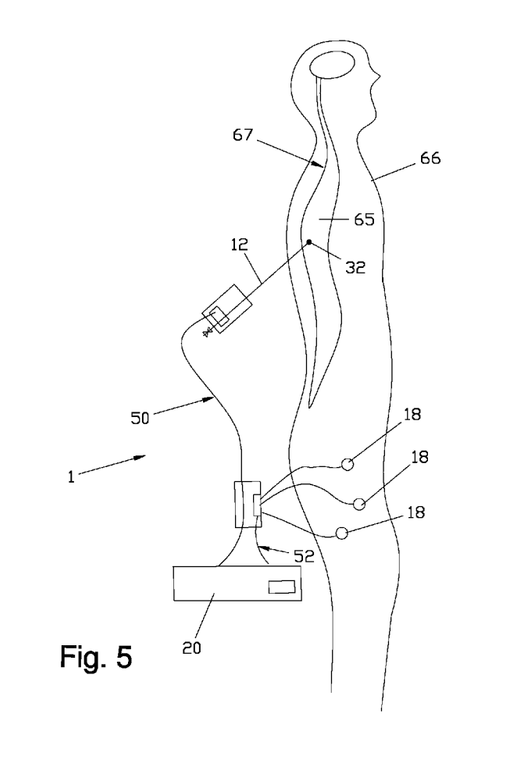
FIGS. 5 and 6 schematically represent two steps of use of the apparatus of FIG. 1.
Figure 6:
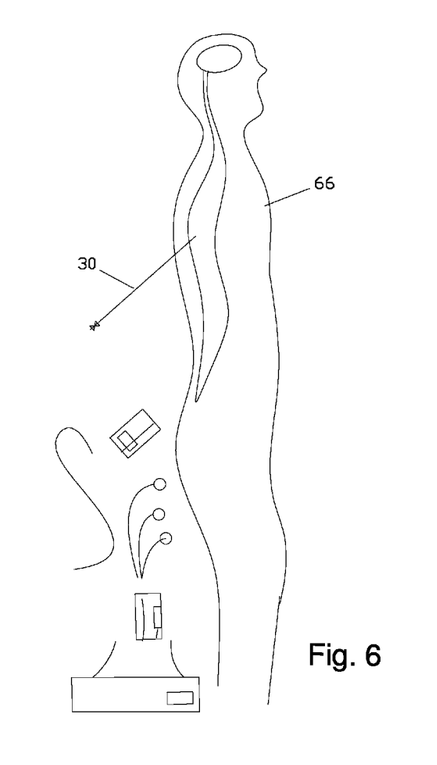

With reference to FIGS. 5 and 6 the use of the apparatus 1 is shown. In particular, FIG. 5 shows a step of insertion of the penetration device 12 in the spinal cord 65 of a patient 66 to position the electrode 32 in contact with its central nervous system 67.

The electrodes 18, on the other hand, are arranged on the skin of the patient in a predetermined position corresponding to the points at which it is possible to read an evoked potential as a consequence of the stimulation of the ganglion that constitutes the target of the subsequent therapy.

In this case, the evoked potential read is a muscle contraction and is translated by the sensors into an electrical signal.

In order to correctly position the electrode 32 at a desired ganglion (not shown) a testing procedure is carried out in which the testing current is sent from the apparatus 20 to the electrode through the first channel 50. Through the second channel 52 the evoked potential is read and a comparison of the reading is provided through the apparatus 20, which in this case therefore has the function of an electromyograph.

When the reading with the electromyograph 20 provides a confirmation signal of the ganglion having been reached, the therapy begins through the delivery of the therapy current through the first channel 50.

Before the start of the therapy it is possible to refine the positioning of the electrode 32 by repeating the position testing with stimulation signals of progressively decreasing magnitude up to a predetermined minimum value.

During the testing step it is useful for the first and the second support element 14 and 16 to be distinct and spaced apart by the section of cable 22, since, in the case of intervention of two operators, one can take care of the catheter and the other the electrical connections and the electromyograph 20. Additionally or as an alternative, the second support element 16 can be rested on the operating table, avoiding an increase in the weight bearing down on the catheter, facilitating the operations of insertion of the "tip" 33 in the patient and making them more precise. Finally, thanks to the cable 22 the other cables and connections are kept far from the sterile field, avoiding contamination.

With reference to FIG. 6, at the end of the stimulation with the therapy current, the catheter 30 is physically disconnected from the other parts of the apparatus 1 and it is left in the body of the patient, so as to be able to be subsequently used as a duct for the administration of drugs.

As already stated, all of the parts described above can preferably physically detach from one another.

At this point it is possible to consider which parts of the apparatus 1 can be considered "consumable portions", i.e. able to be used in a single intervention and necessarily needing replacement or sterilization for the next intervention.

Firstly, it is possible to consider the entire electrocatheter 10 to be consumable material.

From this observation the man skilled in the art will realise that not all of the connections to physically attach and detach the various parts are necessary. For example, notwithstanding the need to attach and detach the catheter 30 to/from the first interface element 14, all or some of the remaining parts of electrocatheter 10 can be permanently connected together and separable only from the apparatus 20.

In the case in which the consumable material is just the assembly of the catheter 30 and its support element 14 (and possibly the cable 22), it is necessary for them to be separable from the remaining elements that overall can, on the other hand, for example, be inseparable from each other (i.e. all that which is located below the line B in FIG. 1 forms a single inseparable part of the equipment).

According to a preferred variant, the elements to the right of the line C (FIG. 1), i.e. the sensors 18, can be separable, for example to be adapted to the type of reading to be carried out.

Of course, no type of connection or separation between the parts can be ruled out.

It should be observed in general that the points of physical and/or electrical coupling and decoupling between the parts can also be in different points from what is described, for example along the electrical connection cables instead of at their ends, and in a different number from what is shown.

Hereafter we will describe some alternative embodiments of the invention where elements that are the same or similar will be indicated with the same reference numerals used above, or with the same numerals increased by 100 or by a multiple thereof.

Figure 7:
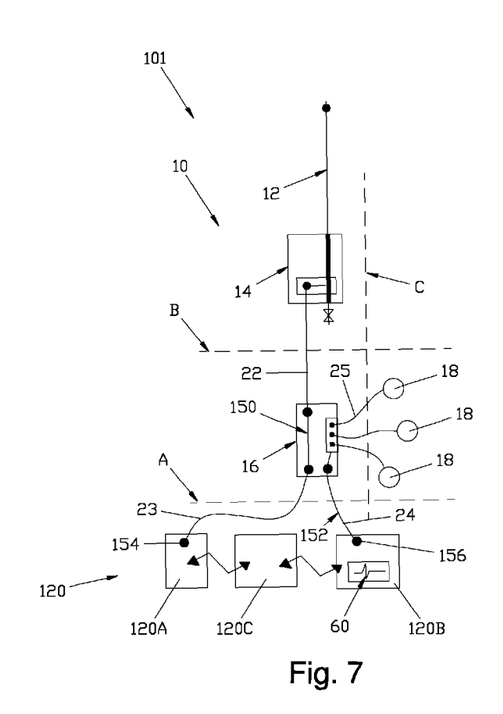
FIGS. 7 to 11 schematically represent respective alternative embodiments of the apparatus of FIG. 1.

With reference to FIG. 7, an apparatus 101 according to the invention is shown that differs from the previous apparatus 1 solely for the fact that the apparatus 120 is made up of two distinct apparatuses, in particular a power supply device 120A, capable of delivering both the testing current and the therapy current to the first channel 150 (and for this reason also called therapy and testing current generating device), and an electromyograph 120B, capable of reading the evoked potential corresponding to the testing current through the second channel 152.

The channels 150 and 152 thus differ from the previous channels 50 and 52 in that the respective ports 154 and 156 belong to distinct devices.

Preferably, the power supply device 120A and the electromyograph 120B are operatively connected together (for example through a data processing device 120C) to allow the generation of an all clear signal 60 to start the therapy that takes into account the comparison between the testing current and the evoked potential. The data processing device 120C can be distinct from the power supply device 120A and from the electromyograph 120B or can coincide with one or both of them.

Figure 8:
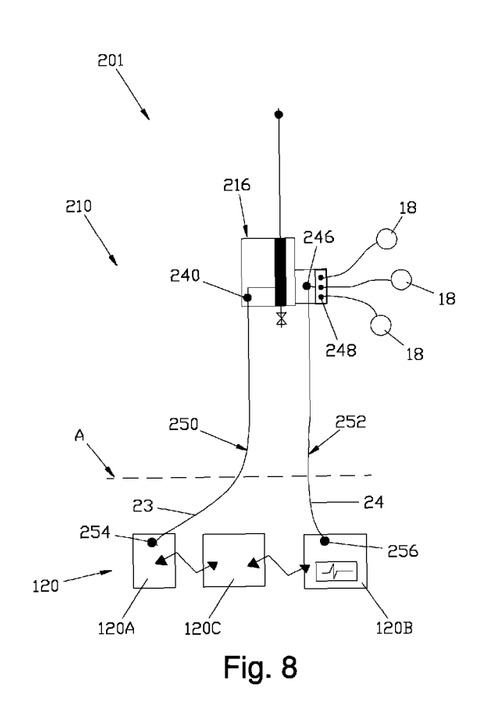

With reference to FIG. 8, an apparatus 201 according to the invention is shown that differs from the previous apparatus 101 solely for the fact that in the electrocatheter 210 the two support elements are joined in a single support element 216 that acts as "physical connection and electrical ramification point" between the parts.

It comprises the port 240 for direct communication with the power supply device 120A, through the first channel 250 that in this case comprises the cable 23 and the port 254. It also comprises the port 246 for the connection with the electromyography 120B, through the second channel 252, which in this case comprises the cable 24 and the port 256.

Figure 9:
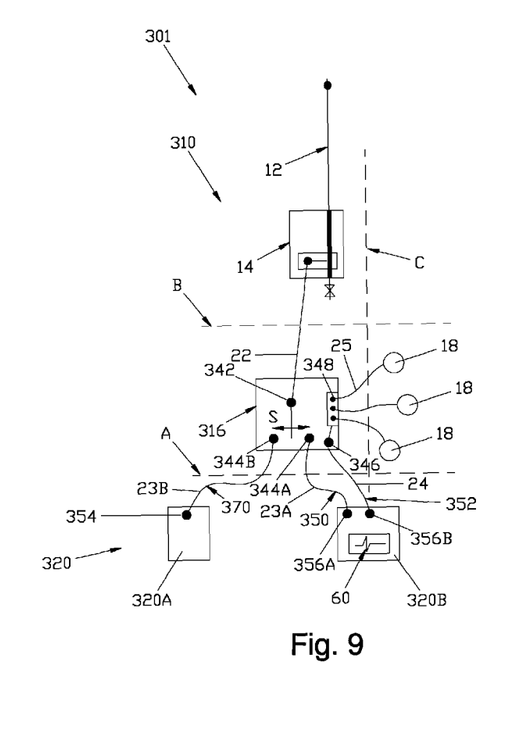

With reference to FIG. 9, an apparatus 301 according to the invention is shown that differs from the previous apparatus 101 solely for the fact that the testing current is generated directly by the electromyograph 320B (therefore also called testing current generating device), whereas the therapy current is generated by the power supply device 320A (therefore also called therapy current generating device).

In order for this to be possible there is a electrocatheter 310 in which the second interface element 316 is a switch capable of allowing or excluding the electrical connection of the catheter 30 with the device 320A and with the electromyograph 320B, respectively. The second interface element in this case can also be called "selector" 316 and can in general be present in any embodiment to join, into a single channel directed to the at least one electrode 32 on the tip of the electrocatheter, the therapy and testing channels coming from the device(s) capable of generating the therapy and stimulation signals.

Going back to the specific case of FIG. 9, the interface element 316 comprises a first and a second port 344A and 344B, where the first is a port intended for supplying the catheter 30 with the therapy current, and the second is intended to supply it with the testing current. The two supply ports can in turns be placed in electrical contact with the outlet port 342 through the switch S.

The interface element 316 also comprises the reading port 346 to forward the signal corresponding to the reading of the evoked potential to the electromyograph 320B.

The electromyograph 320B in turn comprises a supply port 356A and a reading port 356B, respectively connected to the ports 344A and 346 by the cables 23A and 24, respectively.

The first channel 350 for supplying the catheter in this case comprises the port 356A of the electromyograph, the cable 23A, the interface element 316 with its inlet and outlet ports 344A and 342 and the cable 22.

The second reading channel 352, on the other hand, comprises the second port 356B of the electromyograph, the cable 24, the interface element 316 with its inlet and outlet ports 348 and 346 and the cables 25.

Both of the channels 350 and 352 are therefore connected to the electromyograph 320B.

The supply with therapy current, on the other hand, follows a third channel 370, comprising the port 354 of the power supply device 320A, the cable 23B, the interface element 316 with its inlet and outlet ports 344B and 342, and the cable 22.

Of course, variants of this embodiment are also considered in which the supply channels 350 and 370 are totally distinct, i.e. where there is no switch S and where the first interface device has two ports, one for each channel.

Figure 10:
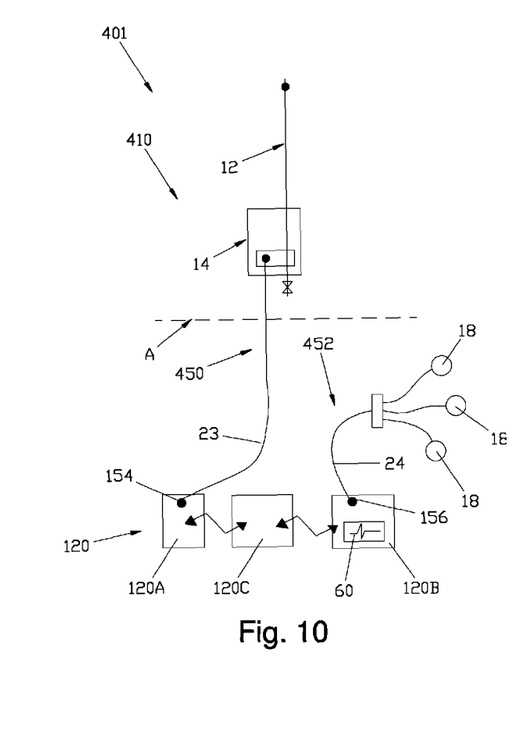

With reference to FIG. 10, an apparatus 401 according to the invention is shown that differs from the previous apparatus 101 solely for the fact that the power supply device 120A and the electromyograph 120B are always physically separate from one another, whereas they are preferably in communication to generate the all clear signal 60.

In particular, in this embodiment there is a electrocather 410 in which the second interface element is missing, so that the cable 23 directly connects the power supply device 120A with the first interface element 14. The supply channel 450 thus comprises the port 154, the cable 23 and the first interface element 14, whereas the second channel comprises the port 156 and the cable 24.

Figure 11:
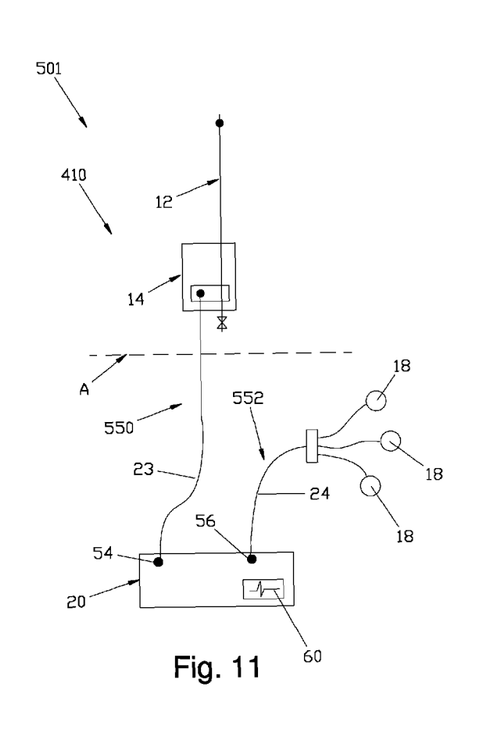

With reference to FIG. 11, an apparatus 501 according to the invention is shown that differs from the previous apparatus 401 solely for the fact that the power supply device and the electromyograph are replaced by a single device 20 having the same functions and the two distinct supply and reading ports 54, 56. In this case the two channels 550 and 552 have a physical joining point given by the device 20.

In general, it should be observed that thanks to the present invention it is possible to implement a procedure for refining the positioning of the electrocatheter or electroneedle in which initially a predetermined stimulus is applied, if a response of the patient is not obtained the electrocatheter or electroneedle is repositioned until a response is obtained, then after a response has been obtained one or more stimuli are applied in succession, each weaker than the last, each time the electrocatheter or electroneedle is possibly repositioned until a response to the stimulus is obtained before passing to a subsequent weaker stimulus. The procedure ends when a response is obtained with a predetermined minimum stimulus. The responses are taken here to mean a printout that indicates that the target has been reached relating at least the reading of the actual response with the magnitude of the stimulus, and possibly with the response time.

It should be observed that the present detailed description has been made with reference to an evoked potential reader, in this case an electromyograph, however the type of reader and therefore the response to the stimulus read can be of any type.

It should also be observed that the power supply devices (current generators) in general are meant to mean devices that transform mains current into therapy and/or stimulation current, however this does not rule out generator devices not supplied by mains current.

Of course, the embodiments and the variants described and illustrated up to now are purely examples and a man skilled in the art, in order to satisfy specific and contingent requirements, can bring numerous modifications and variants, including for example the combination of said embodiments and variants, all of which are in any case covered by the scope of protection of the present invention as defined by the following claims.

The invention claimed is:

1. Apparatus for electrical therapies comprising at least one electrocatheter (10, 210, 310, 410), or an electroneedle, and at least one power supply device (20, 120A, 320A) capable of electrically supplying the electrocatheter or electroneedle with at least one current suitable for carrying out at least one therapy, the apparatus comprising at least one system (90) for testing whether at least one desired point of application of the electrocatheter or electroneedle (10, 210, 310, 410) has been reached in the body of a patient, the testing system comprising at least one device for emitting an electric testing current (20, 120A, 320B) with which to electrically supply the electrocatheter (10, 210, 310, 410) or electroneedle before the start of the therapy, and at least one reading device, configured to provide at least one reading (60) of at least one response generated in the patient (66) by the electrostimulation with the electrocatheter (10, 210, 310, 410) or electroneedle through the testing current.

2. Apparatus according to claim 1, wherein said testing system comprises a data processing device (120C) capable of relating the testing current and the reading of the response, generating at least one target reached signal, and an all clear signal (60) for the start of the therapy, when the relationship reaches a predetermined situation.

3. Apparatus according to t claim 1, wherein the processing device analyses and relates also the time taken by the patient to generate the response to the testing current.

4. Apparatus according claim 1, wherein at least one parameter of the electric testing current can be modified within a predetermined range of values.

5. Apparatus according claim 1, further comprising a device for emitting an electric testing current (20, 120A, 320B) and the power supply device (20, 120A, 320A) capable of electrically supplying the electrocatheter or electroneedle with at least one current suitable for carrying out at least one therapy coincide, whereas the two currents have at least one parameter different from each other.

6. Apparatus according claim 1, wherein the electrocatheter (10,210, 310, 410) or electroneedle comprises at least one penetration device (12) comprising at least one penetration end (33) equipped with at least one electrode (32), the apparatus comprising at least one therapy power supply channel (50, 150, 250, 370, 450, 550) intended to carry the testing current from the power supply device to the electrode and at least one reading channel (52, 152, 252, 352, 452, 552) intended to carry at least one piece of reading information of the at least one reading device (20, 120B, 320B).

7. Apparatus according claim 1, wherein the power supply channels (50, 150, 250, 350, 370, 450, 550) and the reading channel (52, 152, 252, 352, 452, 552) are distinct from each other.

8. Apparatus according claim 6, wherein the power supply channels (50, 150, 250, 350, 370, 450, 550) coincide or partially coincide and in which case one or other is enabled through a switch (316, S).

9. Apparatus according claim 6, wherein at least two of the channels are physically joined together at a predetermined point (16, 20, 216, 316) at the penetration device (12) or separated from it by at least a section of electric cable (22, 23, 24).

10. Apparatus according to claim 9, wherein said joining point (16, 20, 216, 316) coincides with a connection and disconnection point that allows a portion of apparatus comprising the penetration device (12) to be physically separated from the remaining part of the apparatus, so as to be replaced or sanitized for each subsequent operation.

11. Apparatus according claim 1, wherein the electrocatheter (10, 210, 310, 410) or electroneedle comprises at least one end (33) intended to penetrate a patient and to support at least one electrode (32) intended to come into contact with the nervous system to be stimulated (67), where said end (33) extends mainly according to a longitudinal direction (L) and comprises at least one opening (36) for dispensing fluids such as to dispense the fluid in said direction of longitudinal extension (L).

12. Apparatus according claim 1, wherein the testing current has at least one of the following characteristics: from 0.01 Volts to 10 Volts, from 1 to 100 mA.

13. Apparatus according to claim 1, wherein the reading device is configured to be placed in a non-peripheral location on the patient.

14. Apparatus according to claim 1, wherein the at least one response is selected from a group of muscular, sweating and bio-humoral responses.

\* \* \* \* \*